United States Patent
Edwards et al.

(10) Patent No.: US 10,111,924 B2
(45) Date of Patent: Oct. 30, 2018

(54) DIETARY SUPPLEMENT FOR THE TREATMENT OF ACID REFLUX AND GASTRO-OESOPHAGEAL REFLUX DISEASE (GORD/GERD)

(71) Applicant: KFSU LTD, Queensland (AU)

(72) Inventors: Gordon Edwards, Queensland (AU); Malcolm Ball, New South Wales (AU)

(73) Assignee: KFSU LTD, Queensland (AU)

( * ) Notice: Subject to any disclaimer, the term of this patent is extended or adjusted under 35 U.S.C. 154(b) by 380 days.

(21) Appl. No.: 15/037,257

(22) PCT Filed: Nov. 10, 2014

(86) PCT No.: PCT/IB2014/065910
§ 371 (c)(1),
(2) Date: May 17, 2016

(87) PCT Pub. No.: WO2015/071811
PCT Pub. Date: May 21, 2015

(65) Prior Publication Data
US 2016/0287657 A1 Oct. 6, 2016

(30) Foreign Application Priority Data
Nov. 18, 2013 (AU) .............................. 2013904443

(51) Int. Cl.
*A61K 36/00* (2006.01)
*A61K 36/899* (2006.01)
*A23L 33/21* (2016.01)
*A61K 9/00* (2006.01)

(52) U.S. Cl.
CPC ............ *A61K 36/899* (2013.01); *A23L 33/21* (2016.08); *A61K 9/0053* (2013.01); *A61K 9/0095* (2013.01); *A23V 2002/00* (2013.01); *A61K 2236/51* (2013.01)

(58) Field of Classification Search
CPC ..................................................... A61K 36/00
USPC .......................................................... 424/725
See application file for complete search history.

(56) References Cited

FOREIGN PATENT DOCUMENTS

| | | |
|---|---|---|
| JP | 2010-116344 A | 5/2010 |
| WO | WO 2013/131124 A1 | 9/2013 |
| WO | WO 2013/131125 A1 | 9/2013 |
| WO | WO 2014/162303 A1 | 10/2014 |

OTHER PUBLICATIONS

International Search Report and Written Opinion prepared by the Australian Patent Office dated Feb. 20, 2015, for International Application No. PCT/IB2014/065910.
El-Serag, HB et al. "Dietary Intake and the Risk of Gastro-Oesophageal Reflux Disease: A Cross Sectional Study in Volunteers." Gut. 2005, vol. 54, pp. 11-17.

*Primary Examiner* — Michael V Meller
(74) *Attorney, Agent, or Firm* — Berg Hill Greenleaf Ruscitti, LLP.

(57) ABSTRACT

Use of dietary fiber material extracted from sugar cane in the manufacture of a food product that is formulated to ameliorate the effects of acid reflux and extended symptoms of gastro-oesophageal reflux disease. The product ameliorates both the acute and long term symptoms of both conditions.

1 Claim, No Drawings

DIETARY SUPPLEMENT FOR THE TREATMENT OF ACID REFLUX AND GASTRO-OESOPHAGEAL REFLUX DISEASE (GORD/GERD)

CROSS REFERENCE TO RELATED APPLICATIONS

This application is a national stage application under 35 U.S.C. 371 and claims the benefit of PCT Application No. PCT/IB2014/06590 having an international filing date of 10 Nov. 2014, which designated the United States, which PCT application claimed the benefit of Australian Patent Application No. 2013904443 filed 18 Nov. 2013, the disclosures of each of which are incorporated herein by reference.

TECHNICAL FIELD

The invention relates to the field of commercial food supplement manufacture. In particular, the invention relates to a dietary supplement, the use of said supplement in the diet of an individual, and the method of manufacture of said supplement.

BACKGROUND OF THE INVENTION

Acid Reflux or Gastro-Oesophageal Reflux (GOR) is a condition suffered by many individuals at some point in their lives, with some estimates suggesting 60-70% of the population suffering from reflux in any 12 month period. A more severe and chronic progression is diagnosed as Gastro-Oesophageal Reflux Disease (GORD; also known as GERD) approximately 60,000 people are hospitalised with severe GORD a year in Australia alone. The Montreal Definition and Classification of GORD is a condition which develops when the reflux of stomach contents causes troublesome symptoms or complications. Contrary to popular belief, people who lead healthy lifestyles are only slightly less likely to develop GORD than people who are overweight or who smoke or drink alcohol heavily.

The diagnosis of GORD is generally set by its cardinal symptoms of heartburn and acid regurgitation, occurring at least weekly. The prevalence of these weekly symptomatic events among adults has been reported to be in the range of 10-20% in the western world, with higher prevalence in recent years. A study ranging over the last 10 years including 80,000 subjects revealed an increase of 47% on weekly events with gender and age being significant factors. The symptoms of GORD are associated with a decreased health-related quality of life and an increased risk of oesophageal adenocarcinoma.

A more detailed description of the primary event in most people with GORD would be refluxed gastric juices causing heart burn, experienced as a painful or burning sensation in the oesophagus with regurgitation of gastric juices also being common. In addition, other symptoms such as chest pain (reflux chest pain) and extra-oesophageal symptoms such as, reflux asthma, reflux cough, and reflux laryngitis may result. Despite the impact of GORD symptoms on an individual's life, many sufferers do not consult a physician and attempt self-medication.

In simple terms, the oesophagus is the tube between the stomach and the pharynx; more specifically it is the portion of the alimentary canal between the pharynx and the stomach. It is about 25 cm long and consists of three parts; the cervical part, from the cricoid cartilage to the thoracic inlet, the thoracic part, from the thoracic inlet to the diaphragm, and the abdominal part, below the diaphragm to the cardiac opening of the stomach. At the junction of the stomach and oesophagus lies the oesophageal sphincter. During digestion the stomach produces strong acids and enzymes (gastric juices). While the inner lining of the stomach has several mechanisms that provide a protective barrier to these gastric juices the oesophagus does not. The lower oesophageal sphincter (LOS) is the valve that prevents gastric juices encountering the oesophagus. When the lower oesophageal sphincter becomes weakened gastric juices can seep upwards into the oesophagus and GORD/reflux symptoms will generally be the result.

Although it is known that a faulty LOS is a common cause of GORD symptoms it is not known why the fault develops. While pregnancy, hiatus hernia, peptic ulcers, asthma, and smoking can be targeted as triggers of reflux there are many sufferers who experience the condition regardless of their lifestyle.

The primary treatments for Acid Reflux and GORD rely on changes to diet as well as various medications. The aim of both diet and medication based treatments is the reduction in stomach acid, reduction in the occupied volume of the stomach to reduce pressure on the oesophageal sphincter, and reduction in the inflammation of the stomach lining and associated acid production that can result.

The medications typically fall into two major categories; they either act on stomach acid or reduce volume pressures. Acid suppressants, such as Histamine2-receptor antagonists, have shown to be effective as they are good anti-inflammatory agents. An inflamed stomach produces more acid. Accordingly, blocking this extra production of acid prevents excessive concentrations and upwards seeping/pressures. Proton pump inhibitors act on the cells in the stomach wall which produce acids to reduce acid production. Prokinetic agents help promote the emptying of the stomach and stop it becoming overfull. Antacids neutralize the acids in the stomach but are not recommended for frequent events as suffered by patients with GORD, as they interfere with overall stomach function if used for long periods of time.

The vast majority of people suffering acid reflux will improve their symptoms through changes to diet. These include elimination of alcohol, chilli and spicy foods, acidic fruit and vegetables (be it liquid drinks or solid foods). Given that all people react differently to foods there is no prescribed reflux friendly diet applicable to all people. It is a process of removing the foods that cause problems for the specific individual that is applied. For periodic sufferers it would be appropriate to say that eliminating the trigger foods and eating less per meal will result in an improvement to the events and symptoms.

Though there are no hard and fast rules as to diet changes for the treatment of Acid Reflux and GORD, it is accepted that certain foods can help reduce symptoms. These include foods that provide a sated palate and discourage overeating (such as Low Glycaemic Index (GI) foods), foods that provide a thickening characteristic to the gastric juices in the stomach (such as foods high in dietary fibre), high pH vegetables and fruits (that act as natural antacids), and especially complex carbohydrates (that require a greater amount of acid to digest than simple foods) have all been shown to have a beneficial effect when regularly included in the diet.

Typically it has been suggested that soluble fibre has the most pronounced benefit for Acid Reflux and GORD due to its ability to absorb stomach acid and promote gastric clearing there is very little evidence that it provides acute relief from symptoms, rather that inclusion in the diet reduces overall incidence over an extended period of time. The benefits of high fibre diets have recently been called into doubt and this may be largely due to the fact that many fibres are either highly processed (such as chemically modified starches) or from non-vegetable sources such as wheat bran and psyllium husk—both from seed).

Accordingly it is an object of this invention to provide high quality dietary fibre source that alleviates the symptoms of Acid Reflux and GORD, either as an acute treatment (taken immediately after an attack) or as a long term relief by inclusion into the regular diet.

SUMMARY OF THE INVENTION

According to one aspect of the invention, there is provided the use of dietary fibre material extracted from sugar cane in the manufacture of a food product that is formulated to ameliorate the effects of acid reflux or GORD conditions.

Preferably, the sugar cane fibre is prepared via a process including the steps of: subjecting the sugar cane material to at least one wet diffusion step to separate sugars from a residual fibre material whilst maintaining nutrient content; and subjecting the residual fibre material to a rapid, low-heat drying process thereby to retain the biologically active molecules in the fibre, and to enhance the water retention properties of said residual fibre product.

There are a number of advantages to using dietary fibre material extracted from sugar cane in the way described above. Firstly, no adverse allergic effects have ever been recorded with this source. This fibre source can improve gut lining health over and above other sources of fibre. As a whole of plant fibre source it more accurately represents whole vegetables than fibre sources generated from grains or chemically manufactured from other sources. It is also high in essential micronutrients and has the ability to protect micronutrients from other foods when consumed in conjunction with a meal.

Sugarcane fibre prepared according to the invention has several advantageous properties compared to incomplete (not whole plant fibres) such as bran, psyllium husk and inulin. The fibre is a true lignose, hemicellulose and cellulose combination, like the total dietary fibres found in most vegetables. Fibre prepared according to the invention may be classed as almost entirely insoluble fibre, using the standard chemical methods of classification, it has many of the properties of soluble fibres such as high water binding capacity (up to 8-10 times by weight) and a prebiotic effect. Also even though insoluble fibres are known to have little or no effect on blood glucose levels, the inventors have observed that, when prepared correctly, sugarcane fibre can lower the GI of most foods that it is either added to directly or consumed with during a meal. This is most likely a combination of the fact that the hemicellulose fraction of the fibre has soluble components that are released during digestion and that when prepared correctly the fibre retains a number of biologically active molecules.

This combination of both soluble and insoluble fibre characteristics and the essentially "whole food" nature of the invention most likely allows for a food profile that more closely mimics an ideal diet.

The invention also allows more flexible product formats to be developed, in particular that allow individuals suffering acid reflux or GORD to have a quick ready to consume and pleasant cure for acute attacks whenever they occur.

Preferably, the wet extraction step is a diffusion extraction, done under relatively low-shear conditions. The optimal wet extraction step temperature is in the range 25° C. to 70° C.

According to another aspect of the invention, there is provided a food product formulated to ameliorate the effects of Acid reflux or GORD over an extended period; said food product containing dietary fibre material extracted from sugar cane, said dietary fibre material preferably having been prepared according to the steps defined above.

According to another aspect of the invention, there is provided a method of treatment of the effects of Acid reflux or GORD over an extended period in an individual by feeding to said individual a food product incorporating dietary fibre material extracted from sugar cane; said dietary fibre material preferably having been prepared according to the method defined above.

Now will be described, by way of particular, non-limiting examples, preferred embodiments of the invention.

DETAILED DESCRIPTION OF THE INVENTION

The current invention takes advantage of the properties of a dietary fibre isolate produced from sugar cane, in such a way that maximised retention and minimal destruction of the bioactive molecules occurs.

The method of preparation of the fibre material from sugar cane is broadly similar to that described in WIPO patent document no. WO2011/035381 by KFSU Pty Ltd, which is incorporated herein by reference. However, the process according to the present invention may be defined as having the following essential features:

1. A sugar cane size reduction step;
2. A relatively 'gentle' aqueous extraction stage that separates the fibre from other sugar cane fractions, including the sugar fraction, without causing degradation of the fibre functionality; and
3. A relatively gentle drying step that minimises degradation of the fibre functionality.

It is preferred that the extraction step be an aqueous diffusion extraction performed at a relatively neutral pH. It is also preferred that the drying step be a rapid vortex drying operation that, as may be achieved via a low temperature, vortex dryer, said dryer to be able to reduce the wet weight of the sugarcane material from 40-80% w/w to less than 10% w/w in 10-30 seconds while not heating the material to a stage that would significantly damage the bio-actives in the plant material.

It is understood that adequate dietary fibre is important to the healthy function of the digestive system. It is also known that dietary fibre levels in the diet can have an influence on the likelihood of development of Acid Reflux and GORD in humans. It is also thought that human diets tend to be deficient in dietary fibre, and/or use fibre sources known to cause allergies and intolerances, such as wheat and psyllium husk.

It is also understood that many fibres that are processed from grains and other 'incomplete' (i.e. not from a vegetable) sources do not significantly aid in the dietary control of blood glucose levels. It is further understood that many sources of fibre that were thought to have a beneficial effect have been shown in recent studies to either be ineffective or to only provide short term benefits.

The invention provides for the use of sugarcane fibre either alone or in the formulation of foods or diets that seek to reduce the risk of development of Acid Reflux or GORD conditions, or which ameliorate the symptoms of those conditions, if acquired. When prepared according to the invention, this fibre source, and the foods incorporating it, has a number of advantages over other fibre sources and food, including that:

It is relatively hypoallergenic;

It contains both insoluble and soluble fibre in beneficial proportions for dietary intake;

It can be prepared in a 'chemical-free' manner and contain no harmful trace elements, unlike fibre from other sources such as chemically modified starch;

It can be prepared in such a way as to retain the micronutrients and active molecules found in the "molasses" component of sugarcane, without the need to extract and purify those components for their biological function;

By lowering the GI of a meal the fibre will have the potential to reduce the volume of food an individual will consume in a single sitting, thereby reducing the occupied volume in their stomach and reduce gastric pressures against the oesophageal sphincter.

The sugarcane fibre provides the property of thickening fluids including gastric juices. This is a positive action that is described in the amelioration of reflux symptoms via whole food consumption such as Aloe Vera preparations.

Prokinetic agents act to improve the stomach emptying rate and reduce stomach occupied volume pressures. The laxative effect of the sugarcane fibre promotes this same action in the body while also improving overall movement of digested foods in the gut.

Other inventions have sought to isolate the various components however the combined effects of the components exceed that of individual extracts. Additionally the "whole food" nature of the products limits side effects and protects from overdose;

It is also known that too much fibre in the diet can have several negative side effects including but not limited to constipation, diarrhoea and bad flatulence. In one embodiment, where the fibre product is added as a supplement to an individual's diet, dietary fibre intake can be more easily controlled.

The embodiments of the invention can take a number of forms, each with several advantages for users.

In this document:

A 'carrier' is a palatable substrate for the sugarcane fibre, which may or may not contain protein or other nutrients; including but not limited to: fruit extracts, broths, purees, dairy products, baked goods; and which may be in solid or liquid form.

'Inert filler' is any product used to increase the bulk size of fibre according to the invention to allow for ease of handling by the user. The filler may contain flavours or nutrients, and other dietary fibres to improve mouth feel, but does not necessarily contribute to the total benefit provided by the invention.

'Pellet' includes any compact form of the invention, including but not limited to:
  A dried pill or tablet in the manner of a vitamin.
  A 'soft lolly' style lozenge that may be used as a treat or as an addition to other foods All of the examples below can optionally be formulated with additional vitamins and bioactive molecules, or sweeteners such as stevia. Preferably any added nutrients would be sourced from natural ingredient so that a "natural" descriptor may be maintained for the final product.

Example 1

In this example, 0.5-2.0 g of the active fibre is added to a flavouring medium and pressed into a pellet. The pellets are prepared at a formulation level such that the dose may be varied according to the patient's requirements to reduce the symptoms of Acid Reflux or GORD without incurring negative effects. The pellet may be taken during an attack or immediately before or after a meal.

Example 2

In this example the active fibre is mixed with a flavoured drink (for example a non-acidic fruit juice or milk) and pasteurised for sterility (1-5 g per 100-250 ml). A drink prepared in this manner is a convenient, ready-to-consume product to be taken to relieve symptoms of Acid Reflux or with meals.

Example 3

In this example the supplement is prepared as an easy-to-measure powder with or without flavours, stabilisers and inert filler, formulated specifically to be combined with water. Specifically, the active fibre could be mixed with a dry flavour component and an inert filler to form easy-to-use granules. The dose (1-5 g) would be in a convenient single-serve sachet or in a multi-dose bulk pack. This example is best suited to allow reduced meal size, as the granules can be mixed with water (thereby allowing less food to be consumed each meal).

Example 4

In this example the supplement is prepared in a solid flavoured meal such as a biscuit or a bar (1-5 g per ready mixed food). Multiple biscuits can be consumed by an individual to provide a specific dosing regimen as needed for their lifestyle. This has two advantages over other delivery systems in that it feels more like a treat for the consumer, and it eliminates the need for liquid, reduces the total volume of the stomach contents (a factor known to contribute to Acid Reflux and GORD). Additionally the increased saliva production may have a complementary effect with the fibre benefits.

Example 5

In this example, five individuals with a history of chronic acid reflux (their full medical history was not provided as to a specific diagnosis of GORD unless stated), were provided with a food manufactured as per the example stated. A review of their experience after beginning treatment using the dietary fibre product was requested and their belief of its positive treatment effect recorded. The subjects use and outcomes are reported below:

Subject 1 [DW]—The subject has medically diagnosed GORD. She has had limited relief from prescribed medications and has suffered from this condition for many years. In November 2012 the subject was advised by their GP to reduce their reliance on these medications.

The subject was recommended to try taking a product according to example 3 for relief from significant GORD related discomfort. The subject started mixing half a table spoon of sugarcane fibre in a small tub of yoghurt and having it for breakfast. Within 2-3 days of commencing use, the subject's symptoms of GORD had reduced significantly. After six months of continuous daily use the subject's symptoms are greatly reduced. When the subject does experience GORD symptoms, they put a teaspoon of Sugarcane fibre in half a glass of water. Within 10 minutes of drinking the water, the subject reported all symptoms are gone.

After continuing use of sugarcane fibre, the subject reports no longer requiring prescription medication to manage GORD.

Subject 2 [AM]—The subject had also suffered some Acid reflux, due to a stomach ulcer, and reported that taking a supplement prepared according to Example 3 alleviated the reflux almost immediately. The subject had been prescribed Nexium to relieve reflux, and found that consuming the supplement according to Example 3 gave a much quicker result. The subject also reported using a variety of fibre mixes in the past e.g. psyllium, oat bran, all bran, Metamucil, Benefibre. They reported that the supplement according to Example 3 produced better results that these, with the added benefit of acid reflux relief.

Subject 3 [DW]—The subject started using a supplement prepared according to Example 3 for months as a means to alleviate their acid reflux and reported finding it to be very effective. The subject had taken antacids and Nexium for the condition previously, however they found the supplement according to Example 3 worked just as well, and possibly quite a bit faster, allowing the subject to feel comfortable quickly.

Subject 4 [written on behalf of; by JS]—The subject was not well at all, complaining of acid reflux, which had troubled her for many years, and any treatment she has been given had not previously been successful. After using the supplement according to Example 3 (1 teaspoon morning and night)

After using the supplement according to Example 3, the subject reported being thrilled that the supplement assisted with the Acid Reflux problem, and also that her general health is so much better and that her sleep is improved.

Subject 5 [GF]—The subject has recently started taking a supplement according to Example 3 to try and alleviate their acid reflux and found that it worked very well for that purpose. The subject had previously taken medication and antacids (Tums, Mylanta) with limited success.

The subject had also previously been taking a fibre product (psyllium husk) and found that that did not contribute to relieving their acid reflux.

The benefits described by the 5 subjects are significant and demonstrate that supplements prepared according to the invention directly counter their symptoms of acid reflux or GORD to provide relief from both chronic and acute events. All subjects have indicated they are certain that the invention is the source of improvement in pathology.

It will be understood by those skilled in the art that the above examples represent merely some of the ways that the invention may be put into effect. Other embodiments may be envisaged that, while differing in some details, nevertheless fall within the scope of the invention.

The claims defining the invention are as follows:

1. A method of treating acid reflux in a human in need thereof consisting essentially of administering therapeutically effective amounts of sugarcane fiber and a component selected from the group consisting of psyllium and bran to effectively treat the acid reflux in the human in need thereof.

\* \* \* \* \*